United States Patent
Rogers et al.

(10) Patent No.: US 6,979,315 B2
(45) Date of Patent: Dec. 27, 2005

(54) PASSIVE FLOW CONTROL DEVICES FOR IMPLANTABLE PUMPS

(75) Inventors: Charles Rogers, Maple Grove, MN (US); Warren Starkebaum, Plymouth, MN (US); Raymond McMullen, Shorewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 15 days.

(21) Appl. No.: 10/052,077

(22) Filed: Jan. 17, 2002

(65) Prior Publication Data

US 2002/0087120 A1   Jul. 4, 2002

Related U.S. Application Data

(63) Continuation of application No. 09/303,004, filed on Apr. 30, 1999.

(51) Int. Cl.$^7$ .............................................. A61M 1/00
(52) U.S. Cl. ................. 604/151; 604/890.1; 604/892.1
(58) Field of Search ................................ 604/151, 156, 604/246–249, 890.1, 892.1, 93.01, 131, 30, 604/250, 31, 32, 34, 65–67

(56) References Cited

U.S. PATENT DOCUMENTS

| | | | |
|---|---|---|---|
| 3,941,126 A * | 3/1976 | Dietrich et al. ................ | 604/80 |
| 4,077,405 A | 3/1978 | Haerten et al. | |
| 4,193,397 A | 3/1980 | Tucker et al. | |
| 4,258,711 A | 3/1981 | Tucker et al. | |
| 4,447,224 A * | 5/1984 | DeCant et al. ................. | 604/67 |
| 4,604,089 A * | 8/1986 | Santangelo et al. ........... | 604/30 |
| 4,696,671 A | 9/1987 | Epstein et al. | |
| 4,828,545 A | 5/1989 | Epstein et al. | |
| 4,838,887 A | 6/1989 | Idriss | |
| 4,865,584 A | 9/1989 | Epstein et al. | |
| 4,898,583 A | 2/1990 | Borsanyi et al. | |
| 4,898,585 A | 2/1990 | Borsanyi et al. | |
| 5,049,141 A | 9/1991 | Olive | |
| 5,100,380 A | 3/1992 | Epstein et al. | |
| 5,267,964 A | 12/1993 | Karg | |
| 5,281,210 A | 1/1994 | Burke et al. | |
| 5,304,126 A | 4/1994 | Epstein et al. | |
| 5,318,515 A * | 6/1994 | Wilk ........................... | 604/30 |
| 5,464,392 A | 11/1995 | Epstein et al. | |
| 5,820,589 A | 10/1998 | Torgerson et al. | |
| 5,839,467 A | 11/1998 | Saaski et al. | |

FOREIGN PATENT DOCUMENTS

| | | |
|---|---|---|
| DE | 196 42 234 C1 | 4/1998 |
| DE | 19642234 | 4/1998 |
| EP | 0039124 | 11/1981 |
| EP | 0079405 | 5/1983 |
| EP | 0 134 614 A1 | 3/1985 |
| EP | 0134614 | 3/1985 |

(Continued)

OTHER PUBLICATIONS

French Search Report; Aug. 28, 2001 (2 pages).

(Continued)

*Primary Examiner*—Manuel Mendez
(74) *Attorney, Agent, or Firm*—Banner & Witcoff, Ltd.

(57) ABSTRACT

An implantable drug delivery device is provided with a passive flow control device is provided in the form of a valve which may assume two flow states. Flow control is achieved by duty cycling the valve using a control module which generates appropriate signals in response to an input telemetry signal corresponding to a desired flow rate. In another embodiment, a passively controlled bolus delivery device is provided to deliver a bolus of drug in addition to normal dosage.

34 Claims, 3 Drawing Sheets

FOREIGN PATENT DOCUMENTS

| | | |
|---|---|---|
| EP | 0254031 | 1/1988 |
| EP | 0342947 | 11/1989 |
| EP | 0420620 | 4/1991 |
| EP | 0424494 | 3/1994 |
| EP | 0860173 | 8/1998 |
| GB | 1506305 | 4/1978 |
| WO | WO 8700758 | 2/1987 |
| WO | WO 91/16091 A1 | 10/1991 |
| WO | WO 9115258 | 10/1991 |
| WO | WO 9938551 | 8/1999 |

OTHER PUBLICATIONS

French Search Report; Oct. 21, 2003; (3 pages).

* cited by examiner

PASSIVE FLOW CONTROL DEVICES FOR IMPLANTABLE PUMPS

This application is a continuation of and claims priority to U.S. application Ser. No. 09/303,004, filed Apr. 30, 1999.

FIELD OF THE INVENTION

The present invention relates to implantable apparatus for delivering beneficial agents, including drugs to a living body. More particularly, the present invention relates to implantable flow control devices for controlling delivery of beneficial agents to a living body.

BACKGROUND OF THE INVENTION

It is known to provide implanted drug infusion pumps to deliver a controlled, sustained dosage of beneficial agent or drug to the living human body. Such infusion pumps are generally classified as fixed rate infusion pumps or variable rate infusion pumps. Fixed rate infusion pumps deliver drug-carrying fluid at a preset flow rate, which cannot be changed after manufacture. Variable flow rate implantable pumps permit adjustment of the flow rate, but only prior to implantation. Readjustment of the flow rate of variable rate pumps requires removal of the pump from the patient's body and related surgery. Because of the surgical intrusiveness typically required for flow rate changes for both fixed rate and adjustable rate pumps, there has developed a trend towards selectable-rate pumps, which permit flow adjustment while the pump remains implanted in the living body.

Flow control in selectable rate pumps, however, is complicated by the need to limit or minimize the power consumption. To this end, there have been efforts to provide passive flow control elements on selectable rate pumps for minimizing power consumption while providing flow control.

For example, U.S. Pat. No. 5,820,589, to Torgerson and McMullen, the subject matter of which is incorporated herein, in its entirety, discloses the concept of an implantable pump, which is provided with a passive regulator in the form of a manifold communicating with a restrictor network, with a number (n) of bi-stable valves with two flow states, or a number (n) of multi-stable valves with a number (m) of flow states. With the bi-stable valve configuration, the combination overall allows for $2^n$ flow rate options. With the multi-stable valves, the system has $m^n$ flow rate options. Ideally, such bi-stable or multi-stable valves, which can be referred to as passive flow rate control elements, would have no requirement for power except during flow state changes. Power is typically provided via RF signal with suitable electronic implements provided on the pump for providing an induced voltage from the RF signal. While such known passive flow control systems provide variability in flow rates, the number of attainable flow configurations is somewhat limited. It would therefore be desirable to provide an implantable pump with a passive flow control system which provides increased adjustability in flow rates over known systems.

In drug infusion applications, it is frequently desirable to provide for the introduction of a drug bolus to the patient. Bolus dosage may be required, for example, when a patient's activity results in increased pain that is not adequately controlled with normal dosage. Known passive control systems do not provide for the administering of a drug bolus. Thus, there is a need to provide an implantable pump with a passive flow control system which permits the metering and delivery of a bolus of drug.

BRIEF SUMMARY OF THE INVENTION

The present invention solves the aforementioned problems and others by providing an implantable drug infusion pump with a passive flow control device with increased variability in flow settings over heretofore known devices. In a preferred embodiment, the invention provides a bi-stable valve which is duty-cycled by a control module to achieve a desired average flow rate over time. The control module provides appropriate signals at appropriate times to open and close the valve to achieve a desired average flow rate over time. A flow restrictor may be provided downstream of the valve as a safety feature to limit flow or to achieve a desired flow rate range.

The invention also provides a drug infusion pump with a passive flow control device which provides for metering and delivery of a bolus of drug. In a preferred embodiment, a flow conduit communicates with the pressurized reservoir and with a first normally closed, bi-stable valve. The first bi-stable valve is in fluid communication with an accumulator for accumulating a bolus of drug. A second bistable valve isolates the drug supply stored in the accumulator from a drug delivery catheter. To meter a drug bolus into the accumulator, a control module provides an appropriate signal to open and close the first valve and permit ingress of a desired amount of drug to the accumulator. The inlet valve is closed after the bolus has accumulated. When a bolus delivery is desired, the control module delivers appropriate signals to the second valve to release the bolus from the accumulator.

BRIEF DESCRIPTION OF THE DRAWINGS

The invention will be described with reference to the drawings, which form a part of this specification. Those of ordinary skill will understand that the invention is not intended to be limited to these exemplary embodiments illustrated in the drawings, of which.

DETAILED DESCRIPTION OF THE INVENTION

Figure 1:
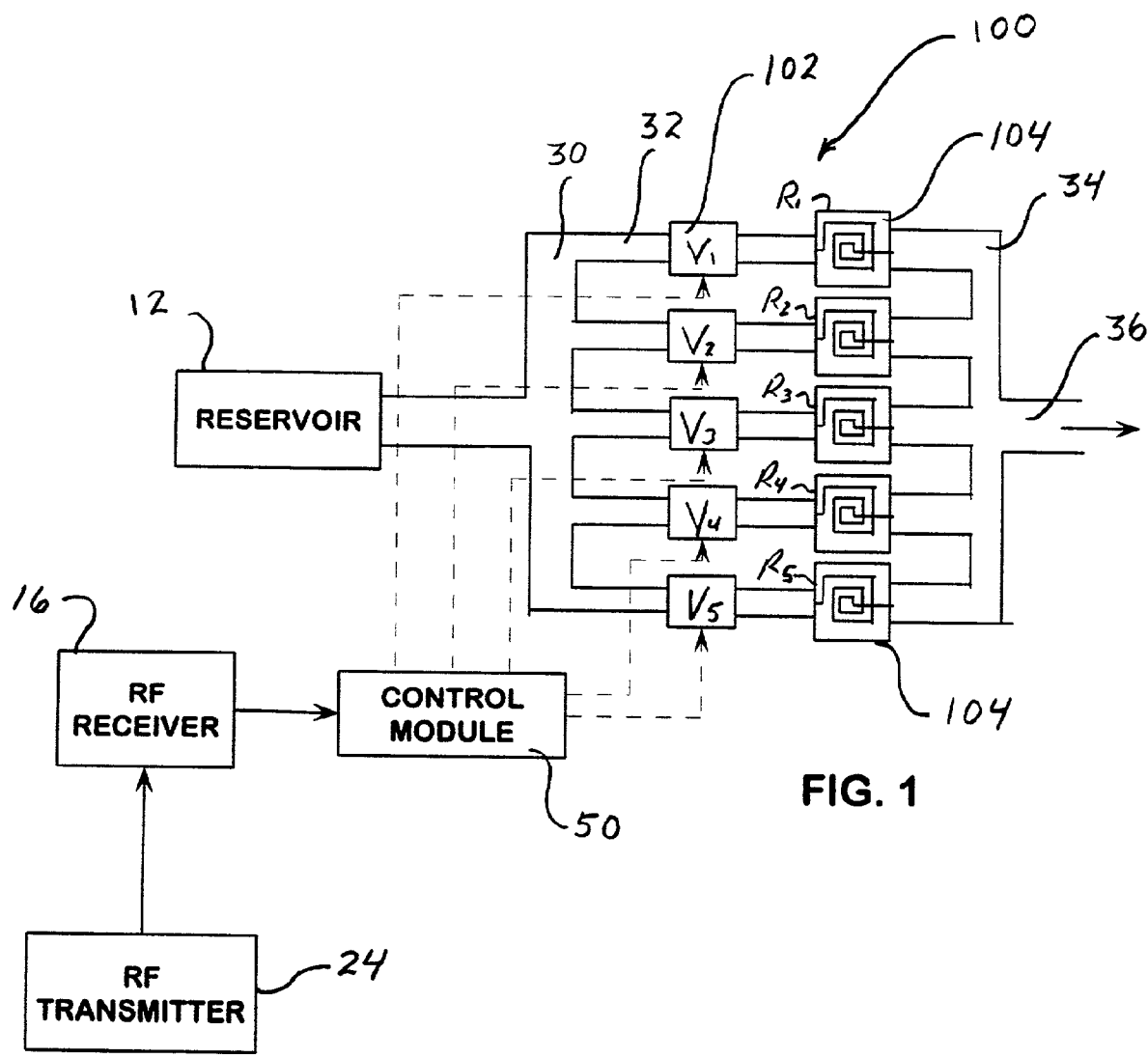
FIG. 1 is a diagrammatic illustration of a fluid control system according to a preferred embodiment of the invention.

FIG. 1 illustrates diagrammatically the components of an implantable pump incorporating a passive flow control device 100 according to a preferred embodiment of the present invention. A pressurized reservoir 12 is provided with beneficial agent in a carrier fluid and communicates with an inlet manifold 30 for conveying fluid to a plurality of inlet branches 32 and a like plurality of valves 102. While five valves are represented in FIG. 1, it will be understood by those of ordinary skill that any number of valves may be provided to achieve a desired range of flow rates. Associated with each valve is a fluid restrictor 104, which is designed to provide a predetermined flow rate, usually proportional to the pressure differential across the restrictor 104. In fluid communication with each restrictor is an outlet manifold 34 which collects the fluid flow exiting each restrictor 104 and conveys the cumulative flow through a delivery conduit 36 to a catheter (not shown) for delivery to a desired location within the body.

In accordance with the invention, each valve V1–V5 is provided with a respective control signal along a signal path from the control module 50. Consistent with known telemetry techniques, control module 50, in conjunction with radio frequency (RF) receiver 16, provides power, in the form of a voltage signal to the respective valves V1–V5. The voltage signals are preferably in the form of impulses of sufficient duration and magnitude to change the state of the valves V1–V5. Control module 50 thus generates respective signals to each of valves V1–V5, based on signals received from RF receiver 16 corresponding to a particular desired one of the available flow rate settings.

In accordance with the invention, the respective flow rates for restrictors R1–R5 are selected to provide a desired range of flows. Typically, a flow rate range between 10 and 2000 μL/day (microliters per day) are practical for most drug administering applications. Preferably, the flow rates of restrictors R1–R5 are related to provide a uniform interval of flow rate increase or decrease for changed states of valves V1–V5. For example, each restrictor may be adapted to provide twice the flow rate of the adjacent and lower flowing restrictor: restrictor R1 may be adapted to provide a flowrate of 10 μL/day, restrictor R2 a flow rate of 20 uL/day, restrictor R3 a flow rate of 40 μL/day, restrictor R4 a flow rate of 80 μL/day and restrictor R5 a flow rate of 160 μL/day. Thus, to achieve a desired range of 10 to 2000 μL/day, with adjustment intervals of 10 μL/day, eight restrictors and corresponding bi-stable valves would be required.

As will be appreciated by those of ordinary skill, the valves 102 of flow control device 100 may be implemented in micromachinery as detailed, for example, in U.S. Pat. No. 5,839,467 to Saaski et al, the subject matter of which is incorporated herein by reference in its entirety. Similarly, restrictors 104 may be provided as micromachined elements or capillary tubes, for example. Alternatively, valves 102 may be macromachined bi-stable elements, including but not limited to solenoid valves, piezoelectric operated valves, or shape memory alloy actuated valves incorporating NITONOL, for example.

Figure 2:
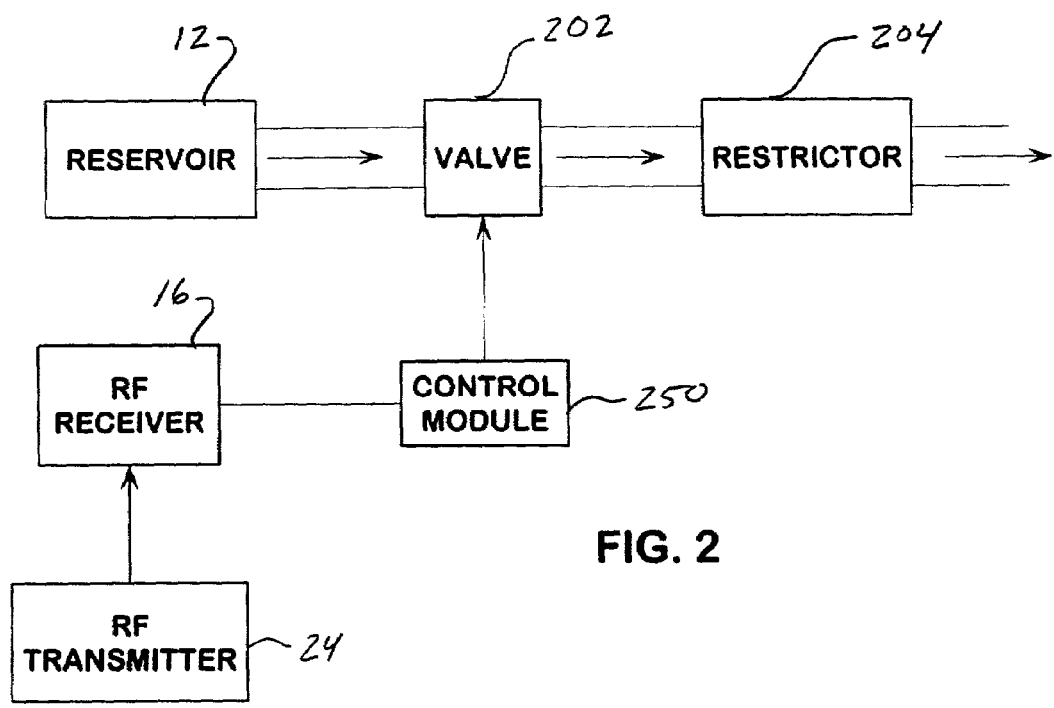
FIG. 2 is a diagrammatic illustration of a fluid control system according to another preferred embodiment of the invention.
Figure 3:
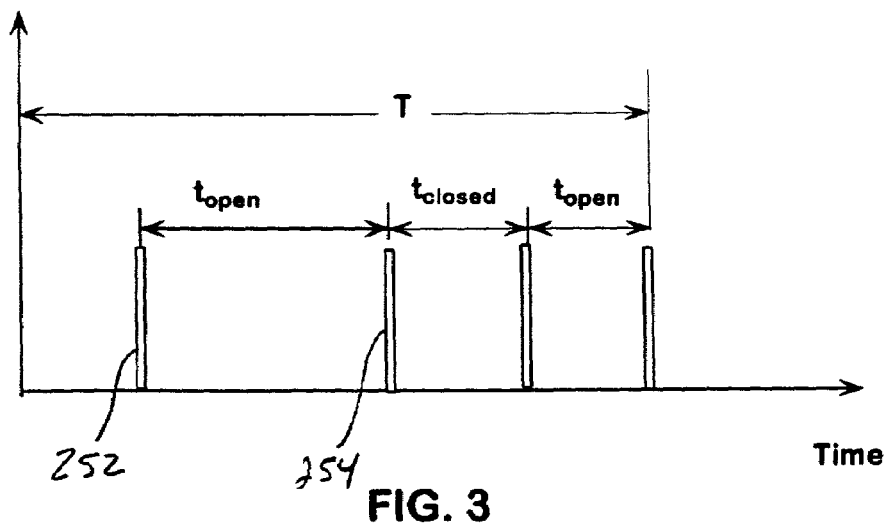
FIG. 3 is a graph of a duty cycling signal associated with the embodiment of FIG. 2.

Referring now to FIGS. 2 and 3, in accordance with another aspect of the invention, a passive flow control device provides for duty cycling a valve 202 to achieve a desired flow rate. Control module 250 is adapted to provides intermittent signals to change to state of valve 202 to achieve desired time-average flow rates. Valve 202 may be a micromachined bi-stable valve as described above with reference to FIG. 1. Valve 202 is capable of being configured to one of two states by an appropriate electrical signal. These two states may correspond to an "open" and "closed" condition, or may correspond to two different flow rates. A flow restrictor 204 may be provided to reduce the flow through valve 202.

In accordance with the present invention, control module 250 provides signals to periodically change the state of valve 202 to achieve a desired flow rate. Referring to FIG. 3, a first signal 252 is provided from control module 250 to change the state of the bi-stable valve to an open-state. For a time period, $t_{open}$, the valve 202 remains open and fluid is permitted to pass at a predetermined rate to the patient's body. Then, after $t_{open}$ has expired, a second signal 254 is sent by control module 250 to change the state of the bi-stable valve 202 to a closed-state, in which the valve 250 will remain for a period $t_{closed}$. In accordance with the invention, the duration of the open and closed states of valve 202 are chosen to achieve a desired average flow rate over a large time interval, T. The flow restrictor 204 may be employed to reduce the flow through valve 202, to thereby provide for more accurate control of the flow rate when the time intervals $t_{open}$ and $t_{closed}$ would otherwise be too small to be accurately controlled by signals from control module 250.

Those of ordinary skill will recognize that a virtually infinite number of average flow rates may be selected by appropriate selection of the duration of time that the valve 202 remains in each of the two states. It will be appreciated that the duty cycling described with respect to FIGS. 2 and 3 may be used in conjunction with a number of valves in a flow control network such as that described above with respect to FIG. 1 while still falling within the scope of the invention described herein.

Figure 4:
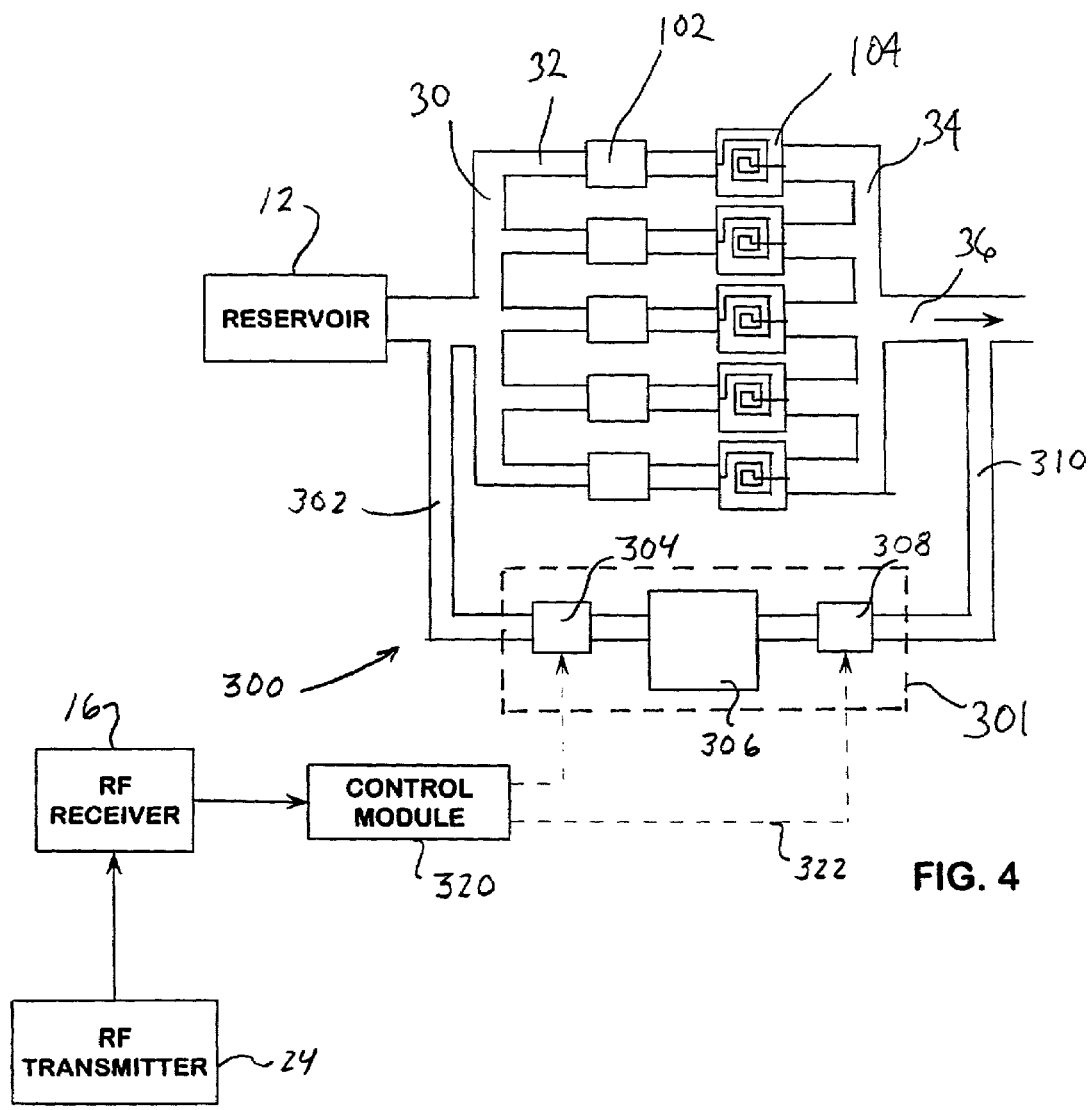
FIG. 4 is a diagrammatic illustration of a fluid control system and bolus delivery device according to another preferred embodiment of the invention.

Referring now to FIG. 4, another aspect of the invention provides a passive flow control system 300 for metering and delivering a drug bolus. The passive flow control system 300 is in parallel communication with the flow control network and specifically the valves of that network described above with respect to FIG. 1. The flow control system includes a bolus delivery component 301 in fluid communication with reservoir 12 that may be employed to meter and deliver a bolus of drug. An inlet passage 302 is provided to direct flow of drug-carrying fluid from the reservoir 12 to an inlet valve 304. An accumulator 306 is in fluid communication with an outlet end of inlet valve 304 to permit the ingress of fluid. An outlet valve 308, is provided at an outlet end of accumulator 306. Inlet valve 304 and outlet valve 308 may be bi-stable valves adapted to remain in their closed positions in the absence of a signal from control module 320.

In operation, upon appropriate telemetry to RF receiver 16 indicating that an operator, or the patient, has requested a bolus of drug, control module 320 provides a first signal to inlet valve 304 to maintain inlet valve 304 in an open state for a predetermined time, corresponding to the amount of drug to be included in the bolus. Under pressure from reservoir 12, drug flows into accumulator. When the predetermined period of time has expired, inlet valve 304 closes. Subsequently, control module 320 initiates a control signal to outlet valve 308 and holds outlet valve 308 in an open state to permit the bolus of drug, which is pressurized within the accumulator, to be delivered to the outlet conduit 310.

Although the preferred embodiment of this invention has been described above in some detail, it should be appreciated that a variety of embodiments will be readily apparent from the foregoing description to persons of ordinary skill. The description is intended to be illustrative of the preferred embodiment of this invention and not intended to be limiting to the scope of protection sought by the applicants, which scope is defined by the appended claims.

What is claimed is:

1. A flow control device for an implantable pump, the flow control device comprising:
   a) a reservoir for containing a pressurized supply of drug and a valve in fluid communication with the reservoir, the valve adapted to assume two flow states;
   b) a control module for generating a control signal to the valve to thereby cause the valve to assume one of the two flow states, the control module duty cycling the valve to achieve a desired average flow rate over time; and c) a bolus delivery component in fluid communication with the reservoir for metering and delivering a predetermined amount of drug bolus, the bolus delivery component further comprising an inlet valve, an accumulator, and an outlet valve, the bolus delivery component in parallel communication with the valve.

2. The flow control device of claim 1, further comprising a flow restrictor in fluid communication with the valve.

3. The flow control device of claim 1, wherein the valve is selected from the group consisting of: micro-machined bi-stable valves, solenoid valves, piezoelectric operated valves and shape memory alloy actuated valves.

4. The flow control device of claim 1, wherein the two flow states comprise and open state, permitting flow through the valve, and a closed state, preventing flow through the valve.

5. The flow control device of claim 1, wherein the valve is a bi-stable valve.

6. The flow control device of claim 1, wherein the bolus delivering component comprises:
(a) the accumulator serving to accumulate the bolus of the medicament;
(b) a first passive flow rate control element for controlling the introduction of the bolus from the reservoir into the accumulator;
(c) a second passive flow rate control element for controlling the exit of the accumulated bolus from the accumulator;
(d) means for controlling the operation of the first and second passive flow rate control elements to allow a predetermined bolus of medicament to accumulate in the accumulator and to allow the accumulated bolus to be released subsequently.

7. The flow control device of claim 1, wherein the accumulator serves to accumulate the bolus of the medicament.

8. The flow control device of claim 1, further comprising an outlet, wherein the valve is positioned between the reservoir and the outlet.

9. The flow control device of claim 1, wherein the control module is further configured to generate a control signal to the bolus delivery component to operatively cause the bolus delivery component to delivery a bolus.

10. A flow control device for an implantable pump, the flow control device comprising:
a) a reservoir for containing a pressurized supply of drug and a valve in fluid communication with the reservoir, the valve being adapted to selectively permit flow of drug at two predetermined rates;
b) a control module for generating a control signal to cause the valve to cycle between the two predetermined rates to achieve a desired average flow rate; and
c) a bolus delivery component in fluid communication with the reservoir for metering and delivering a predetermined amount of drug bolus, the bolus delivery component further comprising an inlet valve, an accumulator, and an outlet valve, the bolus delivery component in parallel communication with the valve.

11. The flow control device of claim 10, further comprising a flow restrictor in fluid communication with the valve.

12. The flow control device of claim 10, wherein the valve is a micro-machined element.

13. The flow control device of claim 10, wherein the two flow states comprise an open state, permitting flow through the valve, and a closed state, preventing flow through the valve.

14. The flow control device of claim 10, wherein the valve is a bi-stable valve.

15. The flow control device of claim 10, wherein the bolus delivering component comprises:
(a) the accumulator serving to accumulate the bolus of the medicament;
(b) a first passive flow rate control element for controlling the introduction of the bolus from the reservoir into the accumulator;
(c) a second passive flow rate control element for controlling the exit of the accumulated bolus from the accumulator;
(d) means for controlling the operation of the first and second passive flow rate control elements to allow a predetermined bolus of medicament to accumulate in the accumulator and to allow the accumulated bolus to be released subsequently.

16. The flow control device of claim 10, wherein the accumulator serves to accumulate the bolus of the medicament.

17. A flow control device for an implantable pump, the flow control device comprising:
a) a reservoir for containing a pressurized supply of drug and a flow control assembly for providing a normal dosage flow rate of drug from the reservoir to a patient, the flow control assembly including a valve in fluid communication with the reservoir and a restrictor in fluid communication with the valve;
b) a bolus delivery component for metering and delivering a predetermined amount of drug bolus in addition to the normal dosage, the bolus delivery component further comprising an inlet valve, an accumulator, and an outlet valve, the bolus delivery device in parallel communication with the flow control assembly; and
c) a control module for providing control signals to the inlet valve and the outlet valve to permit an accumulation of drug within the accumulator.

18. The flow control device of claim 17, wherein the bolus delivery device comprises an accumulator for accumulating a bolus of drug, an inlet valve for selectively permitting ingress of drug to the accumulator, and an outlet valve for selectively permitting egress of accumulated drug from the accumulator.

19. The flow control device of claim 17, wherein the bolus delivering component comprises:
(a) the accumulator serving to accumulate the bolus of the medicament;
(b) a first passive flow rate control element for controlling the introduction of the bolus from the reservoir into the accumulator;
(c) a second passive flow rate control element for controlling the exit of the accumulated bolus from the accumulator;
(d) means for controlling the operation of the first and second passive flow rate control elements to allow a predetermined bolus of medicament to accumulate in the accumulator and to allow the accumulated bolus to be released subsequently.

20. The flow control device of claim 17, wherein the accumulator serves to accumulate the bolus of the medicament.

21. A device for controlling the flow rate of an implantable pump comprising a reservoir adapted to contain a volume of medicament under pressure, the flow rate control device comprising:
(a) a valve in fluidic communication with the reservoir, the valve being adapted to assume two flow states;

(b) a control module for producing a control signal sent to the valve to cause the latter to assume one of the two flow states, the control signal effecting cyclic control of the valve to obtain the desired mean flow rate over time; and (c) a device for passively delivering a controlled bolus in fluidic communication with the reservoir for metering and delivering a predetermined quantity of bolus medicament, the device for delivering the bolus being in parallel communication with the valve.

22. The flow rate control device of claim 21, further comprising a flow restrictor in fluidic communication with the valve.

23. The flow rate control device of claim 21, wherein the valve is selected from the group consisting of; bistable macro-machined valves, electromagnetic valves, piezoelectrically actuated valves, and valves actuated by a shape memory alloy.

24. The flow rate control device of claim 21, wherein the two flow states comprise an open state, which allows flow through the valve, and a closed state, which prevents flow through the valve.

25. The flow rate control device of claim 21, wherein the valve is a bistable valve.

26. The flow rate control device of claim 21, wherein the bolus delivering device comprises:

(a) an accumulator serving to accumulate the bolus of the medicament;

(b) a first passive flow rate control element for controlling the introduction of the bolus from the reservoir into the accumulator;

(c) a second passive flow rate control element for controlling the exit of the accumulated bolus from the accumulator;

(d) means for controlling the operation of the first and second passive flow rate control elements to allow a predetermined bolus of medicament to accumulate in the accumulator and to allow the accumulated bolus to be released subsequently.

27. The flow rate control device of claim 21, wherein the bolus delivering device includes an accumulator serving to accumulate the bolus of the medicament.

28. A flow rate control device for an implantable pump comprising a reservoir adapted to contain a volume of medicament under pressure, the flow rate control device comprising:

(a) a valve in fluidic communication with the reservoir, the valve being adapted to allow a medicament to flow, as selected, at two predetermined flow rates;

(b) a control module for producing a control signal serving to carry out cyclic control of the valve between the two predetermined flow rates to obtain a desired mean flow rate; and (c) a device for delivering a passively controlled bolus in fluidic communication with the reservoir for metering and delivering a predetermined quantity of bolus of medicament, the device for delivering the bolus being in parallel communication with the valve.

29. The flow rate control device of claim 28, further comprising a flow restrictor in fluidic communication with the valve.

30. The flow rate control device of claim 28, wherein the valve is a micro-machined element.

31. The flow rate control device of claim 28, wherein the two predetermined flow rates comprise a first flow rate corresponding to an open state, which allows flow through the valve, and a second flow rate corresponding to a closed state, which prevents flow through the valve.

32. The flow rate control device of claim 28, wherein the valve is a bistable valve.

33. The flow rate control device of claim 28, wherein the bolus delivering device comprises:

(a) an accumulator serving to accumulate the bolus of the medicament;

(b) a first passive flow rate control element for controlling the introduction of the bolus from the reservoir into the accumulator;

(c) a second passive flow rate control element for controlling the exit of the accumulated bolus from the accumulator;

(d) means for controlling the operation of the first and second passive flow rate control elements to allow a predetermined bolus of medicament to accumulate in the accumulator end to allow the accumulated bolus to be released subsequently.

34. The flow rate control device of claim 28, wherein the bolus delivering device includes an accumulator serving to accumulate the bolus of the medicament.

* * * * *